United States Patent [19]

Morrison

[11] Patent Number: 4,992,611
[45] Date of Patent: Feb. 12, 1991

[54] DIRECT CONVERSION OF $C_1$-$C_4$ OXYGENATES TO LOW AROMATIC DISTILLATE RANGE HYDROCARBONS

[75] Inventor: Roger A. Morrison, Deptford, N.J.

[73] Assignee: Mobil Oil Corp., Fairfax, Va.

[21] Appl. No.: 449,170

[22] Filed: Dec. 13, 1989

[51] Int. Cl.$^5$ .............................................. C07C 1/00
[52] U.S. Cl. .................................................. 585/640
[58] Field of Search ........................................ 585/640

[56] References Cited

U.S. PATENT DOCUMENTS

| | | | |
|---|---|---|---|
| 3,894,103 | 7/1975 | Chang et al. | 260/668 R |
| 3,894,104 | 7/1975 | Chang et al. | 260/668 R |
| 3,894,106 | 7/1975 | Chang et al. | 260/668 R |
| 3,907,915 | 9/1975 | Chang et al. | 260/668 R |
| 3,911,041 | 10/1975 | Kaeding et al. | 260/682 |
| 3,928,483 | 12/1975 | Chang et al. | 260/668 R |
| 3,969,426 | 7/1976 | Owen et al. | 260/668 R |
| 4,011,278 | 3/1977 | Plank et al. | 260/668 R |
| 4,397,825 | 8/1983 | Whittam | 423/277 |
| 4,439,409 | 3/1984 | Puppe et al. | 423/328 |
| 4,513,160 | 4/1985 | Avidan et al. | 585/640 |
| 4,547,616 | 10/1985 | Avidan et al. | 585/640 |
| 4,550,217 | 10/1985 | Graziani et al. | 585/408 |
| 4,665,264 | 5/1987 | Rodewald | 585/533 |
| 4,826,667 | 5/1989 | Zones et al. | 423/277 |

FOREIGN PATENT DOCUMENTS 231860 12/1987 European Pat. Off. .
293032 11/1988 European Pat. Off. .

Primary Examiner—Patrick P. Garvin
Assistant Examiner—George R. Fourson
Attorney, Agent, or Firm—Alexander J. McKillop; Charles J. Speciale; Dennis P. Santini

[57] ABSTRACT

A feed containing at least one $C_1$-$C_4$ oxygenate, e.g., methanol, and at least one light olefin, e.g., propylene, is directly converted over a particular zeolite catalyst to a low aromatic distillate range hydrocarbon product.

27 Claims, No Drawings

DIRECT CONVERSION OF $C_1$–$C_4$ OXYGENATES TO LOW AROMATIC DISTILLATE RANGE HYDROCARBONS

BACKGROUND OF THE INVENTION

This invention relates to the direct catalytic conversion of $C_1$–$C_4$ oxygenates, e.g., alcohols, aliphatic ethers and industrial feedstreams containing these and other oxygenated lower aliphatic compounds, to low aromatic content distillate boiling range hydrocarbons. More particularly, the invention is concerned with the direct conversion of a feedstream containing at least one $C_1$–$C_4$ oxygenate, e.g., methanol, and at least one light olefin, e.g., propylene, over the particular zeolite described infra to provide a mixture of low aromatic distillate range hydrocarbons useful as gasoline and/or distillate blending stocks.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. These materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of the==- zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449), zeolite ZS-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

In recent years, considerable research has been devoted to providing alternative sources and manufacturing routes for liquid hydrocarbon fuels in recognition of the fact that petroleum is a non-renewable resource and that petroleum-based fuels such as gasoline and distillate will ultimately become more expensive even should future supplies of petroleum temporarily increase.

The development of fossil fuel conversion processes has enabled the production of oxygenated hydrocarbons from coal, natural gas, shale oil, etc. Synthesis gas ($CO + H_2$) is readily obtained from fossil fuels and can be further converted to lower aliphatic oxygenates, especially methanol (MeOH) and/or dimethyl ether (DME). U.S. Pat. No. 4,237,063 discloses the conversion of synthesis gas to oxygenated hydrocarbons using metal cyanide complexes. U.S. Pat. No. 4,011,275 discloses the conversion of synthesis gas to methanol and dimethyl ether by passing the mixture over a zinc-chromium acid or copper-zinc-alumina acid catalyst. U.S. Pat. No. 4,076,761 discloses a process for making hydrocarbons from synthesis gas wherein an intermediate product formed is a mixture of methanol and dimethyl ether.

Processes for the conversion of coal and other hydrocarbons to a gaseous mixture comprising hydrogen and carbon monoxide, carbon dioxide, etc., ("synthesis gas" or "syngas") are well known. A summary of the technology of gas manufacture, including synthesis gas, from solid and liquid fuels is provided in the "Encyclopedia of Chemical Technology", Edited by Kirk-Othmer, Third Edition, Vol. 11, pages 410–446, Interscience Publishers, New York, NY (1980), the contents of which are incorporated by reference herein.

It has recently been demonstrated that alcohols, ethers and carbonyl-containing compounds can be converted to higher hydrocarbons, particularly aromatics-rich high octane gasoline, by catalytic conversion employing a shape selective medium pore acidic zeolite catalyst such as H-ZSM-5. This conversion is described in, among others, U.S. Pat. Nos. 3,894,103; 3,894,104; 3,894,106; 3,907,915; 3,911,041; 3,928,483; and, 3,969,426. The conversion of methanol to gasoline in accordance with this technology (the "MTG" process) produces mainly $C_5+$ gasoline range hydrocarbon products together with $C_3$–$C_4$ gases and $C_9=$ heavy aromatics. The desirable $C_6$–$C_8$ aromatics (principally benzene, toluene and xylenes) can be recovered as a separate product slate by conventional distillation and extraction techniques. These light aromatics are also produced in a related process for converting methanol to olefins (MTO) as described in, amongst others, U.S. Pat. Nos. 4,011,278; 4,550,217; 4,513,160; and 4,547,616.

U.S. Pat. No. 4,439,409 discloses the use of zeolite termed "PSH-3" therein for the production of hydrocarbons from a feedstock containing methanol and/or dimethyl ether. In the conversion products analyses reported therein, the production of $C_1$-$C_2$ gases was relatively high and notwithstanding patentees' characterization of the conversion product as one of low aromatics content, their analytic data establish that the products nevertheless contain amounts of aromatics exceeding those permissible for a quality distillate product.

SUMMARY OF THE INVENTION

It is an object of the invention to directly convert $C_1$-$C_4$ oxygenates to low aromatic distillate boiling range hydrocarbons useful as gasoline and distillate stocks with minimal production $C_1$-$C_2$ hydrocarbons.

It is a particular object of the invention to directly convert methanol and/or dimethyl ether to low aromatic distillate range hydrocarbons and gasoline with minimal production of $C_1$-$C_2$ hydrocarbons employing as catalyst for the conversion the particular synthetic porous crystalline material, or zeolite, hereinafter described.

By way of achieving these and other objects, the present invention provides a process for converting $C_1$-$C_4$ oxygenates to olefinic hydrocarbons which comprises contacting a feed stream containing at least one $C_1$-$C_4$ oxygenate and at least one light olefin under olefinic hydrocarbon-forming conditions with a synthetic porous crystalline material characterized by an X-ray diffraction pattern including values substantially as set forth in Tables A-D, infra.

It has surprisingly been discovered that when the foregoing conversion is carried out in the absence of light olefin, the resulting product contains a high aromatics content making it unsuitable as a distillate stock. Moreover, the conversion also produces a significant amount of lesser value $C_1$-$C_2$ gaseous hydrocarbons. However, when the oxygenate feed also contains light olefin, the process results in the production of little if any aromatics and $C_1$-$C_2$ gases.

DESCRIPTION OF SPECIFIC EMBODIMENTS

In its calcined form, the synthetic porous crystalline material component employed in the catalyst composition used in the process of this invention is characterized by an X-ray diffraction pattern including the following lines:

TABLE A

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | V-S |

Alternatively, it may be characterized by an X-ray diffraction pattern in its calcined form including the following lines:

TABLE B

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |

TABLE B-continued

| Interplanar d-Spacing (A) | Relative Intensity, $I/I_o \times 100$ |
|---|---|
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE C

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-S |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines:

TABLE D

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of the 2 theta, where theta is the Bragg angle, were determined using algorithms on the computer associated with the diffractometer. From these, the relative intensities, 100 I/$I_o$, where $I_o$ is the intensity of the strongest line or peak, and d (obs.) the interplanar spacing in Angstrom Units (A), corresponding to the recorded lines, were determined. In Tables A–D, the relative intensities are given in terms of the symbols W=weak, M=medium, S=strong, VS=very strong. In terms of intensities, these may be generally designated as follows:

| | | |
|---|---|---|
| W | = | 0–20 |
| M | = | 20–40 |
| S | = | 40–60 |
| VS | = | 60–100 |

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22.

Zeolite MCM-22 has a composition involving the molar relationship:

$$X_2O_3:(n)YO_2$$

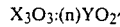

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

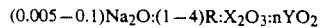

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the alkylation catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for direct conversion of oxygenates to low aromatic distillate. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A–D.

Prior to its use as a $C_1$–$C_4$ oxygenates conversion catalyst, the MCM-22 crystals should be subjected to thermal treatment to remove part or all of any organic constituent present therein.

The zeolite catalyst herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is desired. Such component can be introduced in the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing a platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the $C_1$–$C_4$ oxygenates conversion process of this invention, the zeolite crystals should be at least partially dehydrated. This can be achieved by heating the crystals to a temperature in the range of from about 200° C. to about 595° C. in an atmosphere such as air, nitrogen, etc., and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| YO$_2$X$_2$O$_3$ | 10–60 | 10–40 |
| H$_2$O/YO$_2$ | 5–100 | 10–50 |
| OH$^-$/YO$_2$ | 0.01–1.0 | 0.1–0.5 |
| M/YO$_2$ | 0.01–2.0 | 0.1–1.0 |
| R/YO$_2$ | 0.05–1.0 | 0.1–0.5 |

In a preferred method of synthesizing zeolite MCM-22, the YO$_2$ reactant contains a substantial amount of solid YO$_2$, e.g., at least about 30 wt.% solid YO$_2$. Where YO$_2$ is silica, the use of a silica source containing at least about 30 wt.% solid silica, e.g., Ultrasil (a precipitated, spray dried silica containing about 90 wt.% silica) or HiSil (a precipitated hydrated SiO$_2$ containing about 87 wt.% silica, about 6 wt.% free H$_2$O and about 4.5 wt.% bound H$_2$O of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt.% of SiO2, 8.9 wt.% Na$_2$O and 62.3 wt.% H$_2$O) is used, crystallization may yield little if any MCM-22 crystalline material and impurity phases of other crystal structures, e.g., ZSM-12, may be produced. Preferably, therefore, the YO$_2$, e.g., silica, source contains at least about 30 wt.% solid YO$_2$, e.g., silica, and more preferably at least about 40 wt.% solid YO$_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals based on the total weight of the crystalline product formed.

The zeolite crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the zeolite crystalline material into another material which is resistant to the temperatures and other conditions employed in the C$_1$–C$_4$ oxygenates conversion process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active my change the conversion and/or selectivity of the catalyst. Inactive materials suitably serve as diluents to control the amount of conversion so that C$_1$–C$_4$ oxygenates conversion products, principally olefinic hydrocarbons, can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with zeolite crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

In addition to the foregoing materials, the zeolite crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix may vary widely, with the crystal content ranging from about 1 to about 90 percent by weight and more usually, particularly when the composite is prepared in the form of beads, in the range of about 2 to about 80 weight percent of the composite.

The stability of the zeolite catalyst may be increased by steaming, with suitable steam stabilization conditions including contacting the catalyst with, for example, 5–100% steam at a temperature of at least 300° C. (e.g. 300–650° C.) for at least one hour (e.g. 1–200 hours) at a pressure of 100–2,500 kPa. In a more particular embodiment, the catalyst can be made to undergo steaming with 75–100% steam at 315–500° C. and atmospheric pressure for 2–25 hours.

Among the C$_1$–C$_4$ oxygenates which are suitable for conversion to olefinic hydrocarbons in accordance with the present invention, alcohols and their ethers having the structural formula

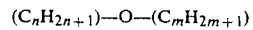

$(C_nH_{2n+1})$—O—$(C_mH_{2m+1})$ wherein n is 1 to 4 and m is 0 to 4 are preferred. Thus, methanol, ethanol, normal propanol, isopropanol, normal butanol, secondary butanol, isobutanol and tertiary butanol can be used either alone or in admixture with one another or in admixture with simple ethers of the above alcohols such as dimethyl ether. Likewise, mixed ethers derived from these alcohols such as methylethyl ether can be used. Especially preferred reactant feeds are methanol, dimethyl ether and mixtures thereof and the above-described compositions which contain at least 10% methanol or dimethyl ether by weight. The feed need not be of greater than ordinary technical purity. Other oxygenated compounds such as esters, and the like, which may be present in the feed will often convert to hydrocarbons along with the alcohols and are therefore to be regarded as useful feedstocks herein.

As indicated above, the feed must contain at least one light olefin, preferably in an amount which is sufficient to effectively direct the overall conversion reaction toward the production of olefin oligomers and away from the production of aromatics and $C_1$–$C_2$ hydrocarbon gases. Olefins which are suitable for this purpose include olefins and mixtures of olefins within the $C_2$–$C_7$ range examples of which are ethylene, propylene, butenes, hexenes, heptenes, mixtures of these and other olefins such as gas plant off-gas containing ethylene and propylene, naphtha cracker off-gas containing light olefins, fluidized catalytic cracked (FCC) light gasoline containing pentenes, hexenes and heptenes, refinery FCC propane/propylene streams, etc. For example, an FCC light olefin stream possessing the following typical composition is entirely suitable for use as co-feed in the process of this invention:

| Typical Refinery FCC Light Olefin Composition | | |
|---|---|---|
| | Wt. % | Mole % |
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.3 |
| Pentanes | 0.7 | 0.4 |

Of the light olefins which can be used herein, ethylene, propylene and the butenes are preferred and of these preferred light olefins, propylene is the most preferred. The propylene (or other light olefin) can be relatively pure or it can be present in gaseous mixtures containing substantial quantities of propylene, e.g., the foregoing FCC light olefin stream. While the amount of light olefin co-feed required to direct the conversion of the entire feed towards olefin oligomer formation will vary on a case-by-case basis, in general, a weight ratio of total light olefin to total $C_1$–$C_4$ oxygenates of from about 0.4 to about 4, and preferably from about 0.6 to about 1.5, will provide good results.

Contact of the mixed $C_1$–$C_4$ oxygenates-light olefin feed with the catalyst in the process of this invention can be carried out by passing the feed through a bed of the catalyst. The catalyst bed can be any of the fixed, fixed fluid, or transported bed types. In a fixed or moving bed operation, the average particle size of the catalyst can be as great as one-half inch or more but is generally between about one-sixteenth and one-fourth inch in diameter. If a fluid bed is employed, the catalyst should be in a finely dived form so that is can be readily fluidized by the lifting action of the feed and diluent vapors. Transport type catalyst beds such as those used in fluid catalytic cracking can also be used.

The effluent from the catalytic conversion step is treated by conventional means to segregate the mixture of product olefinic hydrocarbons to the desired degree, this depending on the specific intended use of one or more of the products.

Reaction conditions are not particularly critical. In general, good results can be achieved with temperatures of from about 500° to about 1000° F., preferably from about 600° to about 850° F., a pressure of from subatmospheric to about 50 atmospheres and preferably from about atmospheric to about 30 atmospheres and a liquid hourly space velocity (LHSV) of from about 0.1 to about 100 hr$^{-1}$ and preferably from about 0.2 to about 50 hr$^{-1}$.

In order to more fully illustrate the $C_1$–$C_4$ oxygenates conversion process of this invention and the manner of practicing same, the following examples are presented. In examples illustrative of the synthesis of zeolite, whenever sorption data are set forth for comparison of sorptive capacities for water, cyclohexane and/or n-hexane, they are Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor, or 40 Torr of n-hexane or 40 Torr cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt.% for water vapor, greater than about 4.5 wt.%, usually greater than about 7 wt.% for cyclohexane vapor and greater than about 10 wt.% for n-hexane vapor. These vapor sorption capacities are a notable distinguishing feature of zeolite MCM-22.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

EXAMPLE 1

Sodium aluminate (43.5% $Al_2O_3$, 32.2% $Na_2O$, 25.6% $H_2O$), 1 part, was dissolved in a solution containing 1 part 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

| | | |
|---|---|---|
| $SiO_2/Al_2O_3$ | = | 30.0 |
| $OH^-/SiO_2$ | = | 0.18 |
| $H_2O/SiO_2$ | = | 44.9 |
| $Na/SiO_2$ | = | 0.18 |
| $R/SiO_2$ | = | 0.35 | where R is hexamethyleneimine.

The mixture was crystallized in a stainless steel reactor, with stirring, at 150° C. for 7 days to produce the zeolite of the invention. The crystalline product was filtered, washed with water and dried at 120° C. After a 20 hour calcination at 538° C., the X-ray diffraction pattern contained the major lines listed in Table E. The sorption capacities of the calcined material were measured to be:

| | |
|---|---|
| $H_2O$ | 15.2 wt. % |
| Cyclohexane | 14.6 wt. % |
| n-Hexane | 16.7 wt. % |

The surface area of the calcined zeolite was measured to be 494 $m^2/g$.

The chemical composition of the uncalcined material was determined to be as follows:

| Component | Wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$ mole ratio = | 21.1 |

TABLE E

| Degrees 2-Theta | Interplanar d-Spacing (A) | $I/I_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were analyzed by X-ray diffraction, sorption, surface area and chemical analyses and the results are presented in Table F. The sorption and surface area measurements were of the calcined product.

TABLE F

| Example | 3 | 4 | 5 |
|---|---|---|---|
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine were added to a solution containing 1 part of sodium aluminate, 1 part of 50% NaOH solution and 44.19 parts of $H_2O$. To the combined solution was added 8.54 parts of Ultrasil silica. The mixture was crystallized with agitation at 145° C. for 59 hours and the resultant product was water washed and dried at 120° C.

Product chemical composition, surface area and adsorption analyses results were as set forth in Table G:

TABLE G

| Product Composition (uncalcined) | |
| --- | --- |
| C | 12.1 wt. % |
| N | 1.98 wt. % |
| Na | 640 ppm |
| $Al_2O_3$ | 5.0 wt. % |
| $SiO_2$ | 74.9 wt.% |
| $SiO_2/Al_2O_3$, mole ratio | 25.4 |
| Adsorption, wt. % | |
| Cyclohexane | 9.1 |
| N-Hexane | 14.9 |
| $H_2O$ | 16.8 |
| Surface Area, $m^2/g$ | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3g samples of the calcined material were ion-exchanged with 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| | Exchange Ions | | |
| --- | --- | --- | --- |
| Ionic Composition, wt. % | TEA | TPA | La |
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

| | |
| --- | --- |
| $SiO_2/B_2O_3 =$ | 6.1 |
| $OH^-/SiO_2 =$ | 0.06 |
| $H_2O/SiO_2 =$ | 19.0 |
| $K/SiO_2 =$ | 0.06 |
| $R/SiO_2 =$ | 0.30 | where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| | |
| --- | --- |
| $H_2O$ | 11.7 wt. % |
| Cyclohexane | 7.5 wt. % |
| n-Hexane | 11.4 wt. % |

The surface area of the calcined crystalline material was measured (BET) to be $405^2/g$.

The chemical composition of the uncalcined material was determined to be as follows:

| | |
| --- | --- |
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio = | 1406 |
| $SiO_2/(Al + B)_2O_3$, molar ratio = | 25.8 |

EXAMPLE 12

A portion of the calcined crystalline product of Example 11 was treated with $NH_4Cl$ and again calcined. The final crystalline product was tested in the Alpha Test and found to have an Alpha Value of 1.

EXAMPLE 13

This example illustrates another preparation of the present zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| | |
| --- | --- |
| $SiO_2/B_2O_3 =$ | 12.3 |
| $OH^-/SiO_2 =$ | 0.056 |
| $H_2O/SiO_2 =$ | 18.6 |
| $K/SiO_2 =$ | 0.056 |
| $R/SiO_2 =$ | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
| --- | --- |
| $H_2O$ | 14.4 wt. % |
| Cyclohexane | 4.6 wt. % |
| n-Hexane | 14.0 wt. % |

The surface area of the calcined crystalline material was measured to be $438 m^2/g$.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio = | 249 |
| $SiO_2/(Al + B)_2O_3$, molar ratio = | 28.2 |

EXAMPLE 14

A portion of the calcined crystalline product of Example 13 was tested in the Alpha Test and found to have an Alpha Value of 5.

EXAMPLES 15-17

These examples illustrate the use of the zeolite of the invention to catalyze the conversion of a feed made up solely of methanol and as such are outside the scope of this invention and are presented for purposes of comparison only. The methanol feedstock contained 17 wt.% water to simulate crude methanol.

The zeolite employed in these examples was prepared by adding a 4.49 parts quantity, by weight, of hexamethyleneimine was added to a mixture containing 1.00 parts sodium aluminate, 1.00 parts 50% NaOH, 8.54 parts Ultrasil VN3 and 44.19 parts deionized $H_2O$. The reaction mixture was heated to 143° (290° F.) and stirred in an autoclave at that temperature for crystallization. After full crystallinity was achieved, the majority of the hexamethyleneimine was removed from the autoclave by controlled distillation and the zeolite crystals were separated from the remaining liquid by filtration, washed with deionized $H_2O$ and dried. A 65 wt.% zeolite/35 wt.% $Al_2O_3$ catalyst composition was then prepared from the zeolite by extrusion. The material was then dried overnight at 120° C. (250 ° F.), calcined at 480° C. (900° F.) in $N_2$, then air was slowly introduced until there was a 100% air atmosphere. The calcination was completed by raising the temperature to 540° C. (1000° F.) and holding at this temperature for six hours.

The conversion conditions and the results of each of the three conversion operations are set forth in Table H (in which P=paraffins, O=olefins, N=naphthas and A=aromatics) as follows:

TABLE H

| | Example | | |
|---|---|---|---|
| | 15 | 16 | 17 |
| Conversion Conditions | | | |
| Temperature, °F.(°C.) | 712(378) | 750(399) | 650(343) |
| Pressure, psig (kPa) | 300(2170) | 800(5620) | 800(5620) |
| WHSV (based on methanol) | 1.00 | 1.00 | 0.45 |
| Time on Stream, hrs. | 5.50 | 4.80 | 5.20 |
| Product Distribution, Wt. % | | | |
| $C_1$ | 5.05 | 10.49 | 2.95 |
| $C_2$ | 0.49 | 2.37 | 0.48 |
| $C_2=$ | 2.22 | 1.12 | 3.83 |
| $C_3$ | 4.49 | 5.59 | 7.24 |
| $C_3=$ | 9.26 | 8.84 | 10.67 |
| iso-$C_4$ | 0.03 | 0.06 | 0.00 |
| n-$C_4$ | 1.93 | 1.73 | 1.67 |
| $C_4=$ | 8.00 | 7.18 | 13.42 |
| iso-$C_5$ | 2.01 | 1.50 | 0.03 |
| n-$C_5$ | 1.23 | 1.30 | 0.00 |
| $C_5=$ | 0.24 | 0.15 | 0.00 |
| $C_6$ P + N | 8.44 | 6.74 | 4.23 |
| $C_6=$ | 2.11 | 1.29 | 0.40 |
| benzene | 0.09 | 0.06 | 0.03 |
| $C_7$'s P + O + N | 10.39 | 7.17 | 2.65 |
| toluene | 0.16 | 0.27 | 0.11 |
| $C_8$'s P + O + N | 3.24 | 2.68 | 1.94 |
| $C_8$ aromatics | 1.06 | 0.95 | 1.12 |
| $C_9+$ aromatics* | 4.36 | 4.06 | 3.86 |
| $C_{10}+$ aromatics | 2.42 | 2.40 | 2.56 |
| durene | 2.84 | 4.17 | 3.34 |
| $C_{11}$-$C_{12}+$ | 17.53 | 20.41 | 21.53 |
| $C_{13}+$'s | 12.42 | 9.50 | 17.93 |
| CO + $CO_2$, Wt. % | 0.00 | 7.87 | 0.00 |
| dimethylether | 14.17 | 1.91 | 34.70 |
| water | 55.99 | 55.59 | 44.57 |
| hydrocarbons | 21.60 | 31.51 | 10.28 |
| methanol | 7.94 | 3.13 | 10.46 |
| aromatics | 8.83 | 13.17 | 5.19 |
| methanol conversion, Wt. % | 66.18 | 93.04 | 29.24 |
| hydrocarbon recovery, % theoretical | 89.82 | 93.20 | 96.72 |

*The $C_9+$ aromatics might possibly contain trace amounts of olefins.

As these data show, even at low methanol conversions, a relatively large amount of $C_1$-$C_2$ gases (methane and ethane), i.e., 3–13 wt.%, were produced. There was incomplete methanol conversion and use of higher temperatures increased the amount of methanol converted to $C_1$-$C_2$ gases. While the higher carbon numbers of the olefinic portion of the conversion product was within the distillate range, the aromatics content of the $C_9+$ distillate range products was too high for a quality distillate product.

EXAMPLES 18-20

These examples illustrate the conversion process of the present invention in which the feed employed contained methanol and propylene.

The catalyst employed in these examples was made the same way as that employed in Examples 15-17, infra. The conversion condition and the results of each of the three conversion operations are set forth in Table I as follows:

TABLE I

| | Example | | |
|---|---|---|---|
| | 18 | 19 | 20 |
| Conversion Conditions | | | |
| Temperature, °F.(°C.) | 692(367) | 725(385) | 800(427) |
| Pressure, psig | 800(5620) | 800(5620) | 250(1825) |
| WHSV (based on methanol) | 2.00 | 2.20 | 2.20 |
| Time on Stream, hrs. | 4.30 | 6.30 | 3.30 |
| Wt. % methanol and water in the feed | 50.23 | 48.99 | 54.06 |
| Wt. % propylene in the feed | 49.77 | 51.01 | 45.94 |
| Product Distribution, Wt. % | | | |
| $C_1$ | 0.16 | 0.03 | 0.30 |
| $C_2$ | 0.00 | 0.03 | 0.10 |
| $C_2=$ | 0.00 | 0.07 | 0.26 |
| $C_3$ | 5.83 | 5.85 | 5.06 |
| $C_3=$ | 3.93 | 4.16 | 3.90 |
| iso-$C_4$ | 2.95 | 3.23 | 6.43 |
| n-$C_4$ | 0.61 | 0.76 | 1.09 |
| $C_4=$ | 2.60 | 2.71 | 2.61 |
| iso-$C_5$ | 2.79 | 2.79 | 6.89 |
| n-$C_5$ | 1.22 | 1.28 | 1.08 |
| $C_5=$ | 2.27 | 2.34 | 4.00 |
| $C_6$ P + N | 10.02 | 10.40 | 12.55 |
| $C_6=$ | 3.77 | 3.98 | 4.02 |
| benzene | 0.24 | 0.22 | 0.23 |
| $C_7$'s P + O + N | 12.54 | 11.94 | 12.39 |
| toluene | 0.00 | 0.00 | 0.00 |
| $C_8$ P + O + N | 8.30 | 8.44 | 8.04 |

TABLE I-continued

| | Example | | |
|---|---|---|---|
| | 18 | 19 | 20 |
| C<sub>8</sub> aromatics | 0.00 | 0.00 | 0.00 |
| C<sub>9</sub> P + O | 42.78 | 41.76 | 31.06* |
| CO + CO<sub>2</sub>, Wt. % | 0.00 | 0.00 | 0.00 |
| dimethylether | 11.65 | 9.96 | 4.03 |
| water | 23.77 | 20.51 | 31.30 |
| hydrocarbons | 60.43 | 59.61 | 60.04 |
| methanol | 4.15 | 9.92 | 4.63 |
| methanol conversion, Wt. % | 55.35 | 46.40 | 79.27 |
| approximate wt. % propylene conversion | 95.23 | 95.14 | 94.90 |

*Some aromatics are produced at this temperature.

As these data show, the additional presence of propylene in the feed had a dramatic impact on the nature of the conversion products. Aromatization virtually disappeared and almost half of the total hydrocarbon product was non-aromatic distillate range material. At the same time, the production of $C_1$–$C_2$ gases virtually disappeared. It may be noted that under especially severe processing conditions, e.g., at the fairly high temperature employed in Example 20, the presence of light olefin in the feed is incapable of preventing the co-production of significant quantities of aromatics.

What is claimed is:

1. A process for converting $C_1$–$C_4$ oxygenates to olefinic hydrocarbons which comprises contacting a feed stream containing at least one of said $C_1$–$C_4$ oxygenates and an olefin oligomer formation-directing amount of at least one light olefin under olefinic hydrocarbon-forming conditions with a synthetic porous crystalline material characterized by an X-ray diffraction pattern including values substantially as set forth below:

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

2. The process of claim 1 wherein the synthetic porous crystalline material is characterized by an X-ray diffraction pattern including values substantially as set forth below:

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

3. The process of claim 1 wherein the synthetic porous crystalline material is characterized by an X-ray diffraction pattern including values substantially as set forth below:

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

4. The process of claim 1 wherein the synthetic porous crystalline material is characterized by an X-ray diffraction pattern including values substantially as set forth below:

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

5. The process of claim 1 wherein the synthetic porous crystalline material has a composition comprising the molar relationship $$X_2O_3 : (n)YO_2.$$

wherein N is at least about 10, X is a trivalent element and Y is a tetravalent element.

6. The process of claim 1 wherein the synthetic porous crystalline material possesses equilibrium adsorption capacities of greater than about 4.5 wt. % for cyclohexane vapor and greater than about 10 wt. % for n-hexane vapor.

7. The process of claim 5 wherein X is selected from the group consisting of aluminum, boron, gallium and combinations thereof and Y is selected from the group consisting of silicon, germanium and combinations thereof.

8. The process of claim 5 wherein X is aluminum and Y is silicon.

9. The process of claim 1 wherein said synthetic porous crystalline material has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

10. The process of claim 1 wherein said synthetic porous crystalline material has been thermally treated at a temperature up to about 925° C. in the presence or absence of steam.

11. The process of claim 9 wherein said synthetic porous crystalline material has been thermally treated at a temperature up to about 925° C. in the presence or absence of steam.

12. The process of claim 1 wherein the $C_1$-$C_4$ oxygenate is selected from the group consisting of alcohol and ether.

13. The process of claim 1 wherein the $C_1$-$C_4$ oxygenate corresponds to the general formula $(C_nH_{2n+1})-O-H$ wherein n is 1 to 4.

14. The process of claim 1 wherein the $C_1$-$C_4$ oxygenate is selected from the group consisting of methanol and dimethyl ether.

15. The process of claim 1 wherein the light olefin component of the feed contains from 2 to 7 carbon atoms.

16. The process of claim 1 wherein the light olefin component of the feed contains at least one olefin selected from the group consisting of ethylene, propylene, butenes, pentenes, hexenes and heptenes.

17. The process of claim 1 wherein the light olefin component of the feed is gas plant off-gas containing propylene.

18. The process of claim 1 wherein the light olefin component of the feed is naphtha cracker off-gas containing light olefins.

19. The process of claim 1 wherein the weight ratio of total light olefin to total $C_1$-$C_4$ oxygenates is from about 0.4 to about 4.

20. The process of claim 1 wherein the weight ratio of total light olefin to total $C_1$-$C_4$ oxygenates is from about 0.6 to about 1.5.

21. The process of claim 1 wherein the $C_1$-$C_4$ oxygenate is selected from the group consisting of methanol and dimethyl ether and the light olefin component of the feed comprises propylene.

22. The process of claim 1 wherein the conversion conditions include a temperature of from about 500° to about 1000° F., a pressure of from subatmospheric to about 50 atmospheres and a liquid hourly space velocity of from about 0.1 to 100 $hr^{-1}$.

23. The process of claim 1 wherein the conversion conditions include a temperature of from about 600° to about 850° F., a pressure of from about atmospheric to about 30 atmospheres and a liquid hourly pace velocity of from about 0.1 to about 50 $hr^{-1}$.

24. The process of claim 1 carried out under fluidized bed conditions.

25. The process of claim 1 wherein said zeolite is combined with a matrix material.

26. The process of claim 25 wherein said matrix material is selected form the group consisting of silica-containing material, alumina-containing material, zirconia-containing material, titania-containing material, magnesia-containing material, beryllia-containing material, thoria-containing material, and combinations thereof.

27. The process of claim 1 wherein the $C_1$-$C_4$ oxygenate corresponds to the general formula $(C_nH_{2n+1})-O-(C_mH_{2m+1})$ wherein n is 1 or 2 and m is 1 or 2.

* * * * *

UNITED STATES PATENT AND TRADEMARK OFFICE
CERTIFICATE OF CORRECTION

PATENT NO. : 4,992,611

DATED : February 12, 1991

INVENTOR(S) : R.A. Morrison

It is certified that error appears in the above-identified patent and that said Letters Patent is hereby corrected as shown below:

```
Col. 1, line 55,  "the = = " should be --these--.
Col. 1, line 63,  "ZS-20" should be --ZSM-20--.
Col. 2, line 58,  "C₉=" should be -- C₉+ --.
Col. 4, line 17,  "W=S" should be --W-M--.
Col. 8, line 7,   "my" should be --may--.
Col. 9, line 67,  "dived" should be --divided--.
Col. 14, line 19, "405²/g" should be --405m²/g--.
Col. 20, claim 23, line 25, "pace" should be --space--.
Col. 20, claim 25, line 29, delete "zeolite" and insert in
      place thereof --synthetic porous crystalline material--.
```

Signed and Sealed this

Seventh Day of July, 1992

Attest:

DOUGLAS B. COMER

*Attesting Officer*     *Acting Commissioner of Patents and Trademarks*